United States Patent [19]
Metz-Stavenhagen et al.

[11] Patent Number: 5,643,262
[45] Date of Patent: Jul. 1, 1997

[54] DEVICE FOR SPINAL COLUMN

[75] Inventors: Peter Metz-Stavenhagen; Bernd Robioneck, both of New York, N.Y.

[73] Assignee: Howmedica GmbH, Schoenkirchen, Germany

[21] Appl. No.: 457,635

[22] Filed: Jun. 1, 1995

[30] Foreign Application Priority Data

Jun. 4, 1994 [DE] Germany .................. 9409123 U

[51] Int. Cl.⁶ .................................................. A61B 17/56
[52] U.S. Cl. ................. 606/61; 606/60; 606/70; 606/71
[58] Field of Search .................. 606/60, 61, 72, 606/73, 69, 70, 71

[56] References Cited

U.S. PATENT DOCUMENTS

| | | | |
|---|---|---|---|
| 4,611,580 | 9/1986 | Wu | 606/61 |
| 4,987,892 | 1/1991 | Krag et al. | |
| 5,053,034 | 10/1991 | Olerud | 606/61 |
| 5,261,909 | 11/1993 | Sutterlin et al. | 606/61 |
| 5,387,212 | 2/1995 | Yuan et al. | 606/61 |
| 5,468,241 | 11/1995 | Metz-Stavenhagen et al. | 606/61 |

FOREIGN PATENT DOCUMENTS

| | | |
|---|---|---|
| 0159007B1 | 1/1989 | European Pat. Off. |
| 0425783A1 | 8/1990 | European Pat. Off. |
| 0553424A1 | 11/1992 | European Pat. Off. |
| 0558883A1 | 1/1993 | European Pat. Off. |
| 2289164 | 11/1974 | France |
| 3306657C2 | 2/1983 | Germany |
| 8802112.2 | 2/1988 | Germany |
| 2131300 | 11/1983 | United Kingdom |
| WO9101115 | 7/1990 | WIPO |
| WO9009156 | 8/1990 | WIPO |
| WO9315697A1 | 8/1993 | WIPO |

OTHER PUBLICATIONS

German Search Report dated Sep. 6, 1994.

*Primary Examiner*—Michael Buiz
*Assistant Examiner*—Mark S. Leonardo
*Attorney, Agent, or Firm*—Peter C. Richardson; Lawrence C. Akers; Elizabeth O. Slade

[57] ABSTRACT

Device for stabilizing, and/or compressing, and/or distracting certain portions of the spinal column is provided. The device utilizes pedicle screws, and an adapter is provided which may be connected by a screw device to the head of a pedicle screw. A roughened portion of the adapter cooperates with a roughened portion of the pedicle screw head to provide for a non-rotatable connection of the adapter with respect to the pedicle screw. The adapter has a circular opening or a recess for receiving the threaded rod which is fixed to the adapter by a threaded device.

6 Claims, 6 Drawing Sheets

DEVICE FOR SPINAL COLUMN

The present invention relates to devices for stabilizing, and/or compressing, and/or distracting certain portions of the spinal column.

Implants utilizing a so-called distracting rod for correcting the spinal column are conventional. French Patent 2,289, 164, as well as British Patent 2,131,300, disclose hooks provided at the ends of a distracting rod engaging beyond the pedicles of the respective vertebrae. Still further, German 33 06 657 discloses a distracting rod variable in length and to be utilized together with pedicle screws. The pedicle screws are screwed into pedicles of the respective vertebrae and the annular head is slid onto a diminished end of the distracting rod to be fixed thereto by means of a nut.

EP 0 159 007 teaches a pedicle screw including a plate-shaped projection having a serration cooperating with a serrated surface at the end of a distracting rod.

As disclosed in EP 0 452 792, a threaded rod inserted through the annular-shaped head of a pedicle screw is fixed to the pedicle screw head by means of nuts.

According to WO 90/09 156 the head of a pedicle screw is provided with a slot receiving a distracting rod. By means of a fixing screw secured to the head, the distracting rod may be fixed to the head of the pedicle screw.

Pedicle screws are often utilized in devices for stabilizing adjacent vertebrae (for example in EP 0 558883). In that case, the pedicle screws cannot be utilized at the same time to hold a distracting rod. In order to transmit certain forces through a distracting rod, the rod must have a minimum diameter which, however, is in many cases larger than the usual inner diameter of an annular-shaped head of a pedicle screw.

It is an object of this invention to provide a device which can be used for stabilizing or compressing or distracting portions of the spinal column to which pedicle screws may be applied. Another object is a versatile device which provides a connection to a distracting rod at the same time.

These objects are attained by the device of the invention.

According to the invention, a device which can be used for stabilizing, compressing, and distracting (as desired) portions of a spinal column utilizes pedicle screws, each including an annular-shaped head in which at least one side of the head includes a roughened portion, the roughened portion comprises an annular serration, and an adapter is provided which may be connected by screw means to the head of a pedicle screw. A roughened portion of the adapter cooperates with the roughened portion of the head to provide for a non-rotatable connection of the adapter with respect to the pedicle screw. The adapter has a circular opening or a recess for receiving the threaded rod which is fixed to the adapter by threaded means.

The device according to the invention provides the advantage that conventional pedicle screws of standard dimensions may be utilized while a threaded rod of sufficient thickness may be used. There is the further advantage that connecting the rod to the pedicle screws is obtained in a simple fashion as the rod is first mounted in the adapter which is then secured to the head of the pedicle screw. If an adapter must be placed through the head of a pedicle screw, problems might occur when the pedicle screw, or, respectively, the head thereof is not aligned with respect to the axis of the threaded rod which is movable to a limited extent.

Preferably, the adapter is dimensioned to be relatively short, including substantially two portions such as a mounting portion to be connected to the pedicle screw head and a receiving portion having an opening for receiving the threaded rod. Still further, the adapter is shaped such that the axis of the bore receiving the threaded rod is normal to the axis of the pedicle screw head.

There is a variety of embodiments to fix the adapter to the pedicle screw head. One embodiment of the present invention provides a threaded bore in the adapter for securing the pedicle screw head by means of a head screw. The mounting portion of the adapter may be thus relatively flat contacting the flat side of the pedicle screw head wherein the mounting portion is provided with a roughened portion cooperating with the roughened portion of the pedicle screw head. An obtuse angle between the receiving portion and the mounting portion of the adapter may be provided such that the receiving bore of the adapter is located substantially above the head of the pedicle screw.

According to another aspect of the invention, the adapter includes a threaded shank portion to be inserted through the head of the pedicle screw and to be secured by means of a nut screwed on the threaded portion. In this case the receiving portion may include a roughened portion cooperating with the roughened portion of the pedicle screw head. Instead of providing the roughened portion at the receiving portion, according to a further embodiment of the invention, a washer may be provided which washer is non-rotatably, but axially, slidably located on the threaded portion to be tightened to the pedicle screw head by means of a nut. The washer has a roughened portion cooperating with the roughened portion of the pedicle screw head.

Moreover, for securing the threaded rod to the adapter, a variety of structures is conceivable. According to a preferred embodiment of the invention, the adapter includes a fixing screw for axially locking the threaded rod in the bore of the adapter.

According to another embodiment of the invention, the adapter is secured to the threaded rod by two nuts, one located at either side of the adapter. According to another embodiment, the threaded rod has a flattened portion or the like to non-rotatably, but axially slidably receive a washer including a roughened portion at one side thereof which is urged towards the roughened portion of the adapter by the nut. The threaded rod preferably includes a pair of reversed threaded portions and a tool-engaging profile, preferably centrally located to exert a tensioning action when rotating the threaded rod. Accordingly, adapters located at opposite ends of the rod may be biased apart from each other or, respectively, towards each other in order to provide respective distracting or compressing forces.

Referring now to the drawings.

Figure 1:
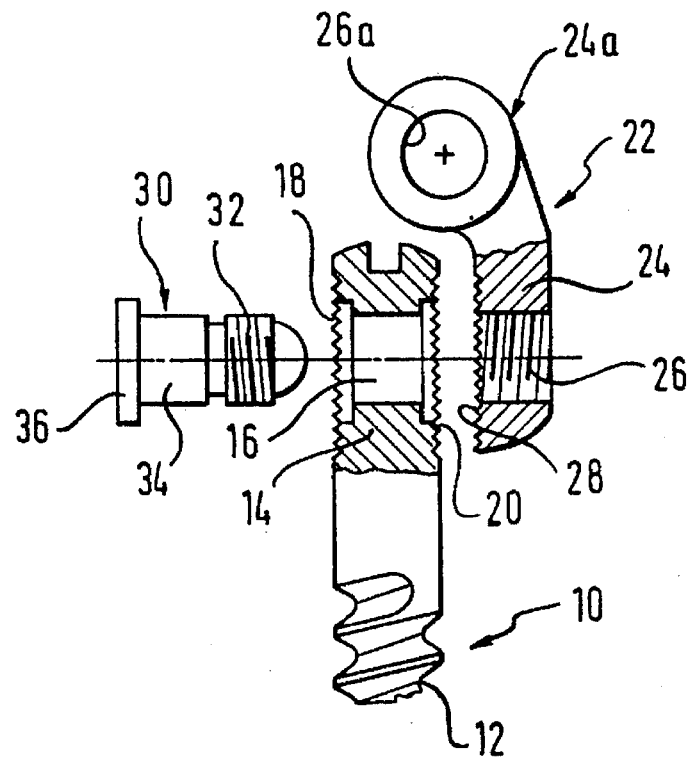
FIG. 1 shows a first embodiment of the spinal device according to the invention, partly in section in which one particular embodiment of an adapter is shown.

FIG. 1 shows a conventional pedicle screw 10 having a screw shank 12 and an annular head 14 including a circular opening 16, as well as serrated faces on opposite sides as seen at 18 and 20. Both ends of the opening 16 are enlarged in diameter. An adapter 22 has a plate-shaped fastening portion 24 and a flat receiving portion 24a which is annular-shaped including a receiving opening 26a. The fastening portion 24 has a threaded bore 26 and a serrated ring face 28. A head screw 30 has a threaded portion 32 as well as a cylindrical portion 34 between the threaded portion 32 and a flange-like head 36. The head screw 30 can be inserted in the opening 16 to be screwed with the threaded portion 32 into the threaded bore 26 to fixedly draw the adapter 22 towards the head 14 of the pedicle screw 10, wherein the serrations engage each other to prevent a rotation of the adapter 22 relative to the head 14 of the pedicle screw 10.

Note that the axis of the receiving opening 26a extends under a right angle to the axis of the threaded bore 26 and, because the fastening portion 24 is angularly located with respect to the receiving portion 24a, the latter is approximately located above the pedicle screw head 14, after the elements are mounted together.

Figure 2:
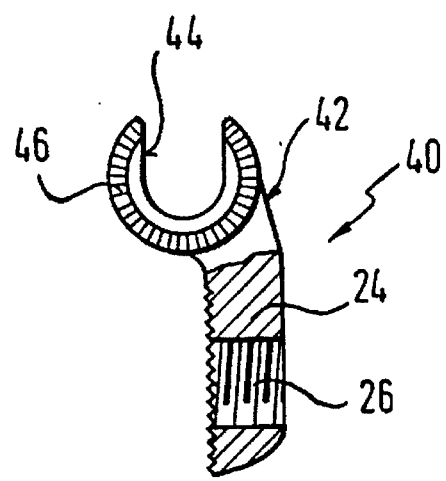
FIG. 2 shows a second embodiment of an adapter, partly in section for use in the spinal device of the invention.

FIG. 2 shows that the adapter 22 may be replaced by an adapter 40 having a fastening portion 24 including a threaded bore 26. The same reference numerals as in FIG. 1 are used. The fastening portion 42 is fork-like and thus includes a recess 44 which is open at the top and which is ringed by a serrated partial ring face 46. The adapter 50 of FIG. 3 has a fastening portion 24 which is similar to that shown in FIGS. 1 and 2. Again, the receiving opening 52 is provided with an annular portion having an annular serration 54 at opposite faces.

Figure 3:
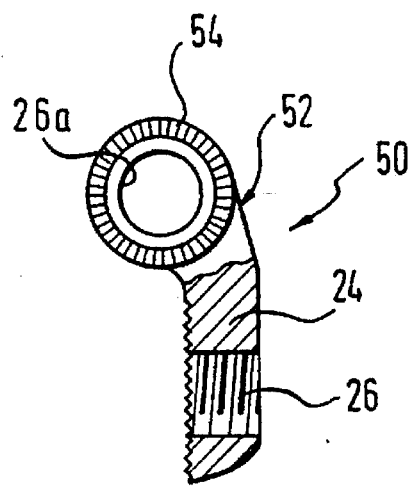
FIG. 3 shows a third embodiment of an adapter for use in the spinal device of the invention.
Figure 4:
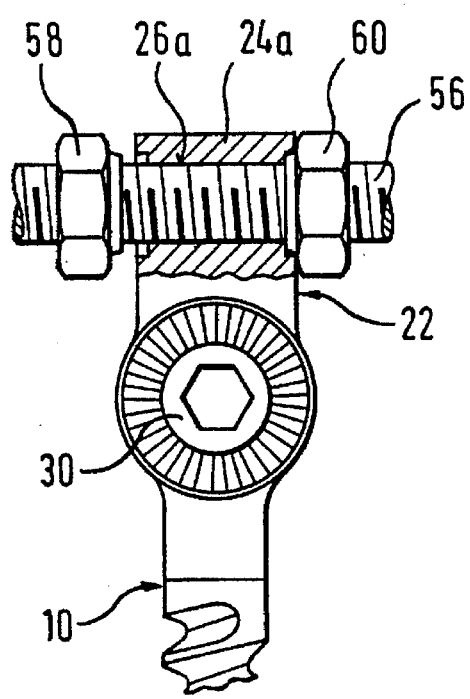
FIG. 4 shows the connection of a threaded rod to the device of FIG. 1.
Figure 5:
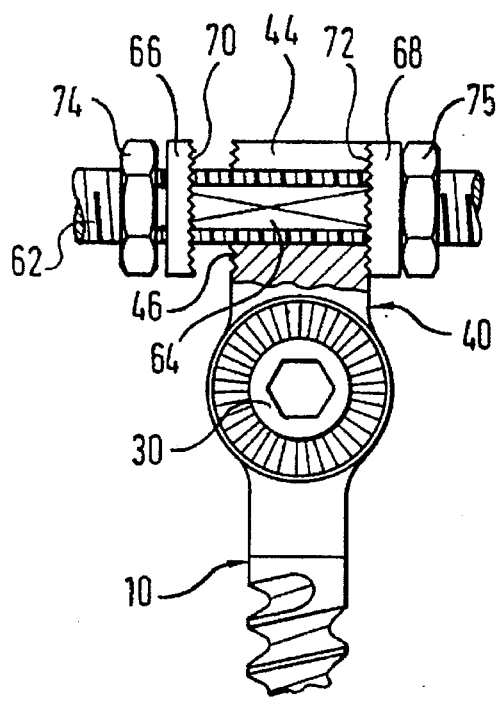
FIG. 5 shows a device similar to the device shown in FIG. 4, but including the adapter of FIG. 2.
Figure 6:
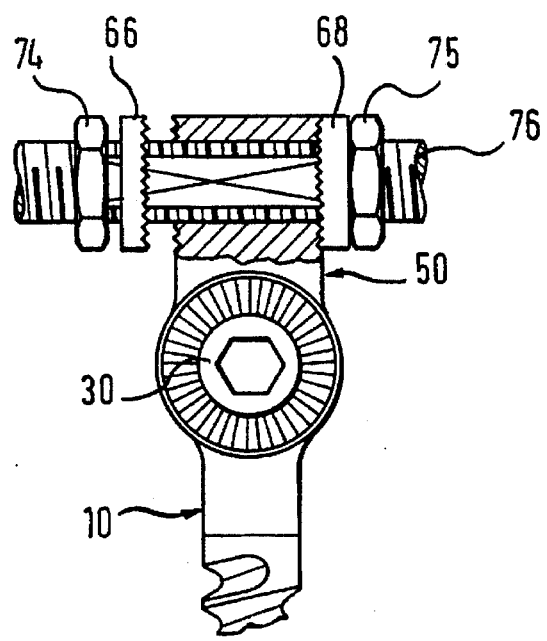
FIG. 6 shows a device similar to the device shown in FIG. 4, but including the adapter of FIG. 3.

FIGS. 4 to 6 show how the embodiments according to FIGS. 1 to 3 respectively cooperate with a threaded rod. By means of the head screw 30 the adapters 22, 40 or 50 are fixed to the pedicle screw 10. FIG. 4 shows how a threaded rod 56 extends through the opening 26a of the receiving portion 24a. The threaded rod 56 is fixed to the adapter 22 by means of nuts 58, 60.

The embodiment shown in FIG. 3 utilizes a threaded rod 62 extending through the opening 26a. The threaded rod 62 includes a flat 64 and carries washers 66, 68 which are non-rotatably, but axially slidably arranged on the rod 62. The washers include a serrated face 70, 72, cooperating with the serration 46 of the adapter 40. The washers 66 and 68 may be secured with respect to the adapter 40 by means of the nuts 74, 76. The washers 66, 68 prevent the rod from being moved out. Still further, they fix the rod 62 against rotation.

The embodiment of FIG. 6 utilizes a threaded rod 76 having a flattened portion also. Again, there are washers 66, 68 and nuts 74, 76 to secure the rod to the adapter 50 in an axial position and fixed against rotation.

Figure 7:
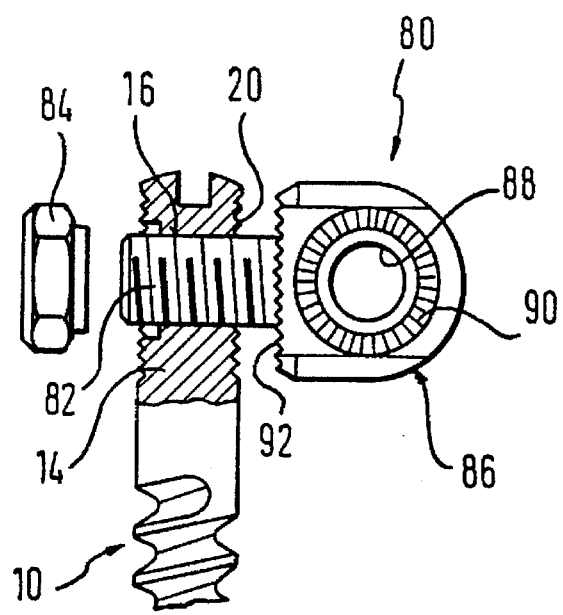
FIG. 7 shows a further embodiment of a spinal device according to the invention.

The embodiment of FIG. 7 shows an adapter 80 having a threaded shank portion 82 which is inserted to the opening 16 of the head 14 of the pedicle screw 10 to be secured to the pedicle screw head 14 by means of a nut 84. The nut has an axial flange engaging the enlarged portion of the opening 16.

The receiving portion 86 of the adapter 80 includes a receiving opening 88 provided for a threaded rod extending therethrough which opening is provided with a serrated annular face 90. The axis of the opening 88 is located normal with respect to the opening 16 in the head 14. The receiving portion 86 has a serrated annular face 92 cooperating with the serrated annular face 20 or, respectively 18 of the screw head 14 as may be seen in FIG. 7.

Figure 8:
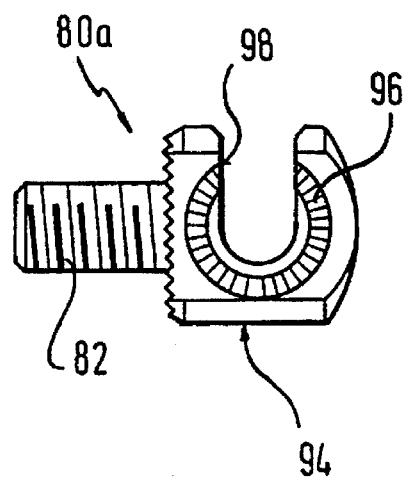
FIG. 8 shows a further embodiment of an adapter for use with the spinal device of the invention.

The embodiment of FIG. 8 shows an adapter 80a having a receiving portion 94 which is fork-shaped and has an annular face section 96 including a serration corresponding to the serrated annular face 90 shown in FIG. 7. The recess has the reference numeral 98.

Figure 9:
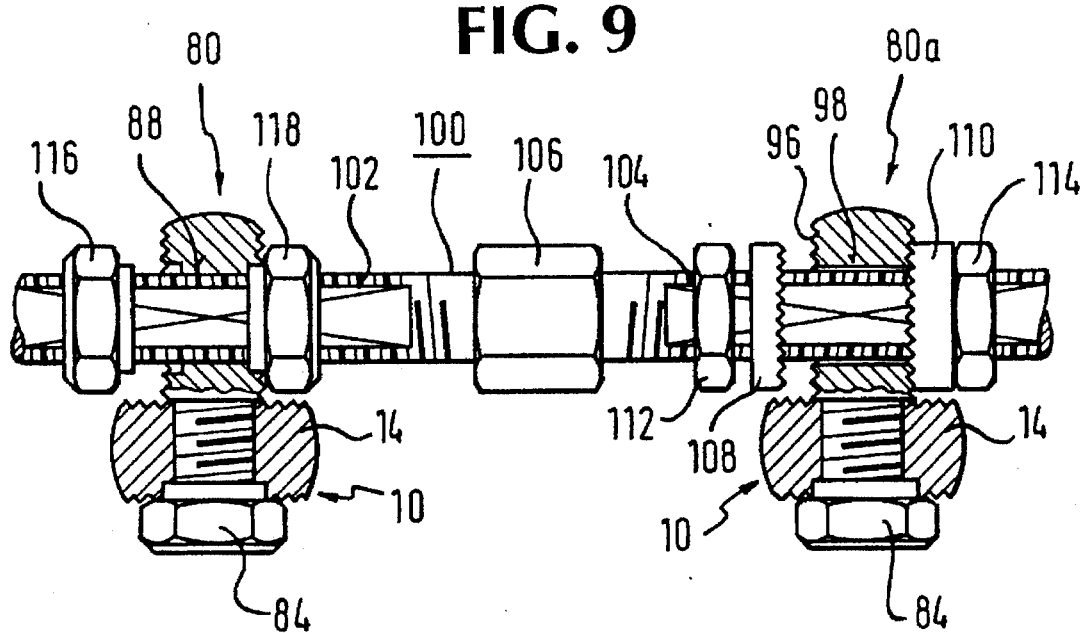
FIG. 9 shows the connection of the devices of FIGS. 7 and 8 to a threaded rod.

According to the embodiment shown in FIG. 9, the threaded rod 100 is provided with threaded portions 102, 104 reversed with respect to each other, wherein a central hexagonal portion 106 is provided which may be engaged by a tool for rotating the rod 100 (for distracting or compressing). The portions 102, 104 of the rod are provided with flattened portions. Washers 108 having serrated head faces 110, respectively, are non-rotatably arranged on the threaded portion 104 to the right end of the rod, and may be secured to the correspondingly serrated annular faces 96 of the adapter 80a by means of nuts 112, 114. The adapter 80 shown in FIG. 9 is connected to the rod 100 merely by means of the nuts 116, 118 having axial flanges cooperating with an enlarged portion within the opening 88.

Figure 10:
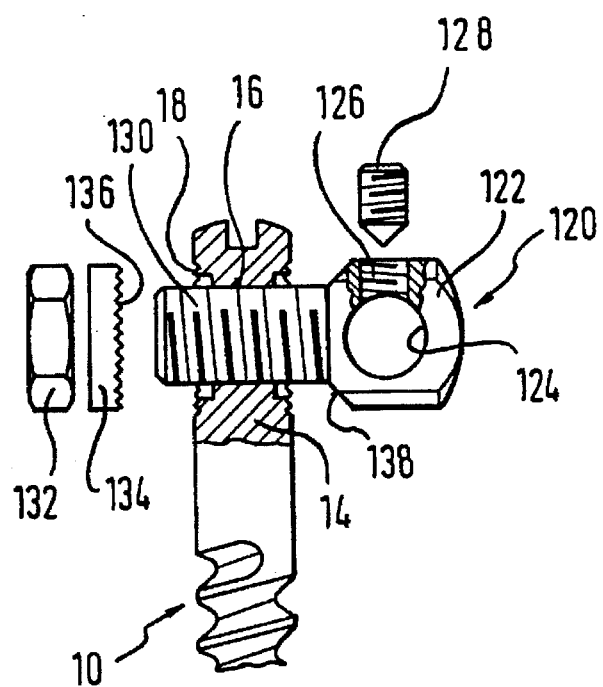
FIG. 10 shows a further embodiment of a spinal device according to the invention.
Figure 11:
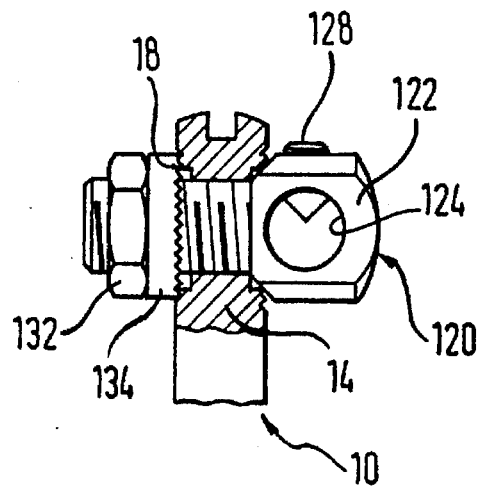
FIG. 11 shows the device of FIG. 10 in assembled and tightened condition.

The embodiment of FIG. 10 and FIG. 11 shows an adapter 120 having a receiving portion 122 including a through-bore 124, wherein the receiving portion 122 has a threaded bore 126 for receiving a fixing screw 128. The mounting portion of the adapter 120 is defined by a threaded portion 130 which is inserted through the opening 16 of the screw head 14 to be provided with a serrated annular washer 134 and a securing nut 132. The threaded portion 130 may be provided with a flattened portion cooperating with a corresponding flattened portion of the washer 134 to non-rotatably secure the adapter 120 to the head 14. As may be seen, the washer including its serration 136 cooperates with the serration 18 of the head 14 of the pedicle screw 10. The receiving portion 122 has a tapered side wall 138 cooperating with the side portion of the head 14.

Figure 12:
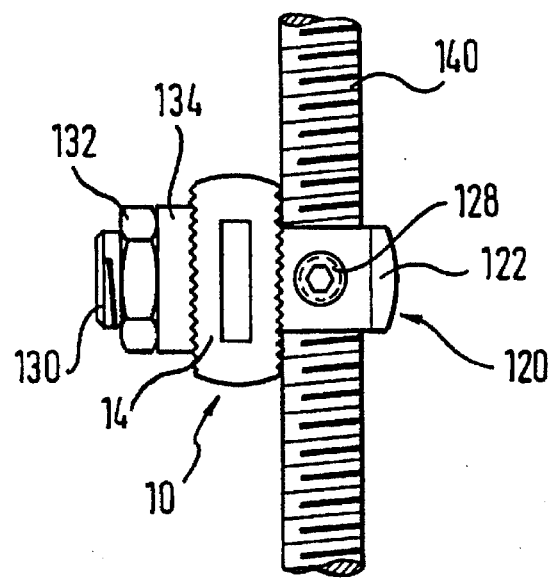
FIG. 12 shows the device of FIGS. 10 and 11 including a threaded rod.

FIG. 12 shows how the adapter 120 according to FIGS. 10 and 11 receives and secures a threaded rod 140. The fixing is provided by means of the fixing screw 128 and by tightening the threaded rod to the serration at the head 14 of the pedicle screw 10.

As may be seen, in all embodiments the threaded rod always extends under a right angle with respect to the axis of the opening in the pedicle screw head. The adapter is shaped such that the threaded rod is located relatively close to the head of the pedicle screw to provide a rather compact arrangement.

We claim:

1. A device for fixing in a selected position sections of a spinal column, comprising at least a pair of pedicle screws and a threaded rod to be connected to each pedicle screw, wherein each pedicle screw (10) includes an annular head (14) having a first face and a second face and an aperture therein, which annular head includes a first roughened portion (18,20) on at least one face thereof, wherein an adapter (20,40,50,80,80a, 120) is provided which is secured to the head (14) of each pedicle screw (10) by first screw means which passes through said aperture in said annular head, wherein a roughened portion (28,46,54,92,96) of the adapter cooperates with said roughened portion of the head (14) to counteract a rotation of the adapter with respect to the pedicle screw, wherein the adapter has a first side and a second side and a receiving opening for receiving the threaded rod, wherein the threaded rod is secured to the adapter by second screw means, wherein the adapter (80,80a,120) includes a threaded portion (82,130) which may be inserted through the annular head (14) of the pedicle screw (10) to be secured by means of a first nut (84,132) screwed on said threaded portion, and wherein the adapter (120) includes a tapered clamping face (138) which is non-rotatably and tightly secured to the pedicle screw head (14) when tightening the nut (132), wherein a first washer (134) includes a roughened portion (136) to fixedly engage the roughened portion (18) of one face of the pedicle screw head (14) when the nut (132) is tightened, and wherein the adapter (22,80) is secured by means of a second nut and a third nut (58,80,116,118) to the threaded rod (56,100) at said first side and said second side of the adapter.

2. The device of claim 1, wherein the threaded rod (62,76,100) includes a flattened receiving portion for non-rotatably receiving a second washer (66,68,108,110) which has a roughened portion at one side, which second washer is secured to the roughened portion (46) of the adapter by means of the nut.

3. The device of claim 2, wherein the threaded rod (100) includes first and second portions (102,104) having oppositely threaded portions and wherein the threaded rod (100) is provided with tool engaging faces (106).

4. A device for fixing in a selected position sections of a spinal column, said device comprising:

(a) at least a pair of pedicle screws, each pedicle screw including an annular head, each head having a first face and a second face and an aperture therein and having a first roughened portion on at least one face, (b) an adapter having a second roughened portion, (c) a threaded rod adapted to be connected to each pedicle screw by attachment of said rod to each pedicle screw through said adapter, (d) first screw means which passes through said aperture in said annular head for securing said head of said pedicle screw to said adapter, wherein said second roughened portion cooperates with said first roughened portion so as to prevent rotation of said adapter with respect to said pedicle screw, and wherein said adapter has a receiving opening for receiving said threaded rod, wherein said adapter includes a threaded portion adapted to be inserted through said aperture in said annular head of each pedicle screw and to be secured by means of a nut screwed on said threaded portion, wherein said adapter includes a tapered clamping face which is non-rotatably and tightly secured to said pedicle screw head by tightening said nut, wherein a first washer includes a roughened portion to fixedly engage the roughened portion of said pedicle screw head when said first nut is tightened, and wherein said adapter is secured by means of a first nut and a second nut to said threaded rod at each side of said adapter.

5. The device of claim 4, wherein said threaded rod includes a flattened portion for non-rotatably receiving a second washer which has a roughened portion on one side of said second washer and said second washer is secured to said second roughened portion by means of said nut.

6. The device of claim 5, wherein said threaded rod includes a first portion and a second portion having opposite threading and wherein said threaded rod is provided with tool engaging faces.

* * * * *